United States Patent
Bigalke et al.

(10) Patent No.: US 6,573,241 B1
(45) Date of Patent: Jun. 3, 2003

(54) THERAPEUTIC AGENT FOR THE SUPPRESSION OF SNORING NOISES

(75) Inventors: Hans Bigalke, Hannover (DE); Jürgen Frevert, Berlin (DE)

(73) Assignee: BioteCon Gesellschaft für bio-technologische Entwicklung und Consulting GmbH, Berlin (DE)

( * ) Notice: Subject to any disclaimer, the term of this patent is extended or adjusted under 35 U.S.C. 154(b) by 0 days.

(21) Appl. No.: 09/857,835

(22) PCT Filed: Dec. 10, 1999

(86) PCT No.: PCT/EP99/09791
§ 371 (c)(1),
(2), (4) Date: Jun. 8, 2001

(87) PCT Pub. No.: WO00/33863
PCT Pub. Date: Jun. 15, 2000

(30) Foreign Application Priority Data

Dec. 10, 1998 (DE) .......................................... 198 56 897

(51) Int. Cl.[7] ........................ A61K 38/16; A61P 11/00
(52) U.S. Cl. ........................ 514/12; 514/2; 424/239.1; 435/69.7; 435/252.7; 530/350; 530/412; 530/825
(58) Field of Search .................... 514/2, 12; 424/239.1; 530/350, 412, 825; 435/252.7, 69.7

(56) References Cited

U.S. PATENT DOCUMENTS

| 4,551,473 A | 11/1985 | Schossow |
| 5,512,547 A | 4/1996 | Johnson et al. |
| 5,721,215 A | 2/1998 | Aoki et al. |

FOREIGN PATENT DOCUMENTS

| WO | 94/00481 | 1/1994 |
| WO | 94/28923 | 12/1994 |

OTHER PUBLICATIONS

Nancy Heneson, Deadly toxin calms excited muscles, New Scientist, Dec. 8, 1990.
Peter Hambleton, Chlostridium botulinum toxins: a general review of involvement in disease, structure, mode of action, and preparation for clinical use, Journal of Neurology (1992), 239: 16–20.

*Primary Examiner*—Christopher S. F. Low
*Assistant Examiner*—Chih-Min Kam
(74) *Attorney, Agent, or Firm*—Gudrun E. Huckett

(57) ABSTRACT

In a method of manufacturing a therapeutic agent to be administered intramuscularly for suppressing snoring noises a high-purity Clostridium toxin BoNT/A or TeNT or at least one of a high-purity Clostridium toxin BoNT/B, BoNT/C1, BoNT/D, BoNT/E, BoNT/F and BoNT/G is added to a carrier. In an alternative, one or more hybrid proteins as a Clostridium toxin, having a light subunit of a Clostridium toxin of the following group and a heavy subunit of a different Clostridium toxin of the same following group, which group contains BoNT/A, BoNT/B, BoNT/C1, BoNT/D, BoNT/E, BoNT/F, BoNT/G and TeNT, are added to a carrier. According to another alternative, a complex, containing a Clostridium toxin or a hybrid protein, and further containing one or more therapeutically well-tolerated hemagglutinins and/or pharmaceutically well-tolerated non-toxic proteins, is added to a carrier. The carrier can be an aqueous solution, a saline solution, or liposomes.

16 Claims, No Drawings

THERAPEUTIC AGENT FOR THE SUPPRESSION OF SNORING NOISES

BACKGROUND OF THE INVENTION

Nightly snoring is not only a psychosocial problem. This disorder represents a risk factor for diseases of the cardiovascular system such as hypertension (Kleitmann, 1963; Lugaresi et al., 1983; Hoffstein et al., 1991) and myocardial (Waller and Bhopal, 1989; Koskenvuo et al., 1985) as well as central ischemia (Koskenvuo et al., 1987). Moreover, patients with constricted respiratory tract are especially at risk of developing a sleep apnea which goes hand-in-hand with an increased mortality (He et al., 1988; Hoch et al., 1986).

The soft palate is comprised of the striated muscles *M. tensor veli palatini, M. pterygoideus, M. genioglossus, M. geniohyoideus*, and *M. sternohyoideus*. When breathing in, some of these muscles are activated. The degree of activation depends moreover on some other factors which have not yet been elucidated in detail. A disruption of the interaction of the muscles can cause snoring. One reason for snoring is an increased tone of the *M. tensor veli palatini* during the deep sleep phase. In the REM phase, the muscle tone is lowered and snoring decreases or ceases (Lugaresi et al. 1994). However, when the tension of the muscles is increased, a sounding board is generated which is caused to vibrate as a result of the breathing air passing it. When the vibration frequency is above 20–30 Hz, it becomes audible. The higher the frequency of the vibrations, the higher the pitch of the snoring. The frequency depends on the tension of the muscles: a more strongly tensioned muscle vibrates at a higher frequency than a slightly tensioned one; a relaxed muscle does not vibrate. The volume of snoring correlates with the vibration amplitude which is determined by the speed of the breathing air passing by.

When the pathologically tensioned striated muscles are paralyzed with a long-acting muscle relaxant, the increased muscle tensions during this deep sleep phase are suppressed, and snoring does not occur.

Botulinum toxins of the type A, B, C1, D, E, F, and G (BoNT/X) are strongly effective neurotoxins which induce paralysis of the striated muscles lasting for several weeks (Ahnert-Hilger and Bigalke, 1995). The cause of paralysis is an inhibition of the acetylcholine release from the nerve ends supplying the muscles. The toxins are proteins and are comprised of two subunits of different size which are covalently bonded to one another with a total weight of $M_R$ 150,000. Some of these neurotoxins are embedded in a complex (total weight: $M_R$ 900,000) which is comprised of hemagglutinins and non-toxic proteins (Inoue et al., 1995). Exclusively the presence of the neurotoxin is required for the muscle paralysis, which neurotoxin bonds with its larger chain, i.e., the C-terminal subunit of the toxin, to receptors which are only present at nerve cells. By means of a receptor-induced endocytosis, the toxin is endocyted by the nerve cells. Here, the lighter chains, the N-terminal subunits, cleave cell-own proteins, which play a key role in the fusion of transmitter-containing vesicles with the plasma membrane (Schiavo and Montecucco, 1997). As a result of cleavage the fusion is suppressed, and the release of the transmitter is blocked: the muscle can no longer contract. Several of the cell-own proteins (fusion proteins), which are present in the membranes of secretory vesicles and/or in the plasma membrane, take part in the secretion process or the release. They can also be present in the cytosol. These proteins include SNAP 25, synaptobrevin (VAMP) and syntaxin, respectively, their isomeric forms. These proteins form the so-called fusion complex which fixes the secretory vesicles to the inner side of the plasma membrane. The fixation is preceded by membrane fusion, which is triggered by a tension-inducing $Ca^{++}$ influx. As a result of the inactivation of only one of the fusion proteins, for example, by proteolytic cleavage, the formation of the fusion complex is prevented. The fusion proteins are the target molecules of the light chains of the above-mentioned neurotoxins. For example, BoNT/B, D, F and G cleave VAMP, while BoNT/A, C1 and E deactivate SNAP 25, and Syntaxin is cut by BoNT/C1. VAMP is moreover inactivated by tetanus toxin (TeNT), a poison which also belongs to the group of Clostridia neurotoxins (Ahnert-Hilger and Bigalke, 1995).

BoNT/A is already used therapeutically for the treatment of different forms of local, often very painful, muscle tensions that impair the patient greatly, for example, Torticollis spasmodicus, Blepharospasmus, various spasticities and the like (Cardoso and Jankovic, 1995). The toxin is injected into the respective muscle. After a few days, the muscle is paralyzed. The patient is pain-free and can again fulfill his daily tasks. Undesirable side effects occur rarely and are fully reversible, as are the desired effects.

SUMMARY OF THE INVENTION

An elimination of snoring could be achieved if it were possible to suppress the increased tone of the palate muscles in the deep sleep phase. Since the tone increase is caused by an increased acetylcholine release, the blockage of the release can cause the muscles to relax and can eliminate snoring.

The object of the invention is now solved by therapeutic agents for suppressing snoring noises which are characterized by a Clostridium toxin and/or a complex of this toxin or a contents of toxin or complex.

Accordingly, the invention relates to a therapeutic agent for suppressing snoring noises which is characterized by a high-purity Clostridium toxin BoNT/A.

Accordingly, BoNT/A can be injected in minimal dosage into the respective muscle of the soft palate, for example, into the *M. tensor veli palatini*. With the same injection technology the spasmodic dysphonia is already treated which is also the result of an increased tone of certain muscles of the soft palate (Schönweiler et al., 1998).

Moreover, the invention concerns a therapeutic agent for suppressing snoring noises which is characterized by a high-purity Clostridium toxin BoNT/B, BoNT/C1, BoNT/D, BoNT/E, BoNT/F and/or BoNT/G.

Moreover, the invention relates to a therapeutic agent for suppressing snoring noises which is characterized by a high-purity Clostridium toxin TeNT.

Moreover, the invention relates to a therapeutic agent for suppressing snoring noises, which is characterized by
  (i) a hybrid protein as the Clostridium toxin, comprised of
    a light subunit of a Clostridium toxin of the following group and of a heavy subunit of a different Clostridium toxin of the same following group, comprised of: BoNT/A, BoNT/B, BoNT/C1, BoNT/D, BoNT/E, BoNT/F, BoNT/G and TeNT; or
  (ii) by a mixture of hybrid proteins according to (i).

Moreover, the invention relates to a therapeutic agent which is characterized by a complex, comprising
  (i) a Clostridium toxin or a hybridprotein and
  (ii) one or more therapeutically well-tolerated hemagglutinins and/or one or more pharmaceutically well-tolerated non-toxic proteins.

Moreover, the invention relates to a therapeutic agent which is characterized by a complex of the wild type.

Moreover, the invention relates to a therapeutic agent which is characterized in that the Clostridium toxin is a recombinant protein.

Moreover, the invention relates to a therapeutic agent which is characterized in that the Clostridium toxin is a lyophilized protein.

Moreover, the invention relates to a therapeutic agent which is characterized in that it is present as an aqueous solution, in particular, an aqueous injection solution.

Moreover, the invention relates to a therapeutic agent which is characterized in that the Clostridium toxin or its complex is present as a physiological saline solution.

Finally, the invention relates to a therapeutic agent which is characterized by liposomes as carriers for the Clostridium toxin or its complex.

The administration of the pure neurotoxin is preferred as compared to the injection of the complex because only the neurotoxin provides the activity. Since the neurotoxin has a smaller molecular weight than the complex, it is distributed by diffusion more quickly within the muscle tissue, binds on receptors, and inhibits the acetylcholine release after it has been endocyted by the nerve end. The other body-foreign proteins would have no own effect with respect to muscle paralysis. However, they would contribute to the stimulation of the immune system because they act as immune adjuvants and enhance the immune reactions. A stronger immune response is desired for inoculations. In the case of a therapeutic agent against snoring, however, an immune reaction could result in the undesirable formation of antibodies which would neutralize the toxin before it could become active in the case of a renewed dosage.

All body orifices, and thus also the nose-throat area, are rich in lymphatic tissue which protects the entryways against damaging substances. When injuries occur and body-foreign substances penetrate in this area, macrophages are attracted which endocyte the foreign substances, digest them and excrete the fragments of the foreign substances with cell-own proteins on their cell surface. In the spleen and other lymphatic tissues, lymphocytes detect the fragments and form immunoglobulins which bind foreign substances freely contained in the tissue and neutralize it.

The degree of attraction of the macrophages depends inter alia on the concentration of foreign substances and the availability of macrophages. The availability of macrophages cannot be influenced, and the palate area is rich in these cells. In order to keep the probability of an immune response minimal, the mass of foreign proteins, i.e., neurotoxin and hemagglutinins must be kept as minimal as possible because macrophages which are attracted in large numbers by non-active foreign substances (immune adjuvants) will, of course, also endocyte the neurotoxin present within the tissue. The mass of the neurotoxin can be reduced by a BoNT with high biological activity to a barely still active dosage. Because the accompanying proteins do not contribute to the desired effect, they can be removed in accordance with the invention.

DETAILED DESCRIPTION OF THE PREFERRED EMBODIMENTS

EXAMPLE 1

An indirect injection with video laryngoscopy was performed on three healthy men sitting upright. Thirty minutes before the toxin injection, atropine sulfate (0.5 mg) was administered subcutaneously in order to suppress saliva secretion. The oropharynx, the mesopharynx, and the larynx were anesthetized surficially with tetracaine hydrochloride (1%) to which had been added adrenaline hydrochloride (1.2 mg) in order to generate a local vessel constriction. Lyophilized, purified BoNT/A (i.e., free of the body-foreign accompanying proteins; BioteCon, Berlin) was dissolved in physiological saline solution p.i. (300 pg/ml). The injection was carried out with a curved cannula with video control. The men were asked to breathe normally during puncturing with the cannula. At three locations of the *M. tensor veli palatini* 100 µl, respectively, were injected in the case of the first test person, 200 in the case of the second, and 300 µl in the case of the third. The dosage of the toxin was thus 50–150 pg/palate which corresponds to 8–25 U. The palette muscles relaxed within 3–5 days. The effect of the toxin was sustained for 3–4 months. After this time period, the snoring noises occurred again, first softly, then increasingly louder.

Subjectively (interview of the partner) as well as objectively, by measurements, a reduction of the snoring was determined. The degree of relaxation of the palate muscle was determined by a frequency analysis of the snoring noises. Depending on the toxin dosage, the frequency of the snoring noises decreased. Moreover, the noise level of the snoring decreased which was the result of an enlargement of the cross-section of the upper respiratory tract. As a result of the enlargement, the flow velocity of the breathing air is reduced so that the amplitude of the vibrations of the soft palate was reduced. Swallowing or speech impairments did not occur.

EXAMPLE 2

As described in regard to example 1, a test person was injected with BoNT/B into the *M. tensor veli palatini*. The total dosage was 15 pg which was distributed to four injection points. The injection volume was 1 ml. The palate muscles relaxed accordingly within 3–5 days. The effect of the toxin was sustained for approximately 6 weeks. After this time period, the snoring noises occurred again, first softly, then increasingly louder.

Subjectively (interview of the partner) as well as objectively, by measurements, a reduction of the snoring was determined. The degree of relaxation of the palate muscles, as already described in example 1, was objectively determined. Swallowing or speech impairments also did not occur after injection of this sub-type.

EXAMPLE 3

As described in example 1, a test person was injected with BoNT/C1 into the *M. tensor veli palatini*. This test person had been treated with BoNT/A complex (BOTOX, Merz GmbH & Co. KG) for several years because of a Torticollis spasmodicus. A year ago (1997) a paralysis of the neck muscles could no longer be triggered, despite doubling the dosage from 150 U to 300 U. Based on this, neutralizing antibodies were found by means of an isolated nerve-muscle preparation (Göschel et al., 1997). In order to relieve even this patient from snoring, he received BoNT/C1. The total dosage was 50 pg which was distributed to four injection points. The increased dosage was required because the type C1 has a reduced specific toxicity in comparison to types A and B. The injection volume was 1 ml. The palate muscles relaxed accordingly within 3–5 days. The effect of the toxin lasted for approximately 14 weeks. After this time period, the snoring noises occurred again, first softly, then increasingly louder.

Subjectively (interview of the partner) as well as objectively, by measurements, a reduction of the snoring was determined. The degree of relaxation of the palate muscles, as already described in example 1, was objectively determined. Swallowing or speech impairments also did not occur after injection of this sub-type.

References

Ahnert-Hilger, G., Bigalke, H.: Molecular aspects of tetanus and botulinum neurotoxin poisoning. Progress Neurobiol. 46: 83–96, 1995.

Cardoso, F., Jankovic, J.: Clinical use of botulinum neurotoxins. Top Microbiol. Immunol. 195: 123–141, 1995.

Göschel, H., Wohifahrt, K., Frevert, J.: et al.: Botulinum A Toxin Therapy: Neutralizing and Nonneutralizing Antibodies—Therapeutic Consequences. Experimental Neurology 14: 96–102, 1997.

He, J., Kryger, M. H., Zorich, F. J., et al.: Mortality and apnea index in obstructive sleep apnea. Chest 94: 9–14, 1988.

Hoch, C. C., Reynolds, C. F. III, Kupfer, D. J, et al.: Sleep disordered breathing in normal and pathologic aging. J. Clin. Psychol. 47: 499–503, 1986.

Hoffstein, V., Mateika, J. H., Mateika, S.: Snoring and sleeping architecture. Am. Rev. Respir. Dis. 143: 92–96, 1991.

Kleitman, N.: Sleep and wakefulness. Chicago, The University of Chicago Press, 1963.

Koskenvuo, M., Kaprio, J., Partinen, M., et al.: Snoring as a risk factor for hypertension and angina pectoris. Lancet i: 893–896, 1985.

Koskenvuo, M., Kaprio, J., Telakivi, T., et al.: Snoring as a risk factor for ischaemic heart disease and stroke in men. Br. Med. J. 294: 16–19, 1987.

Lugaresi, E., Cirignotta, F., Montagna, P., et al.: Snoring: Pathogenic, Clinical, and Therapeutic aspects. In Abnormal sleep. 621–629, 1994.

Lugaresi, E., Mondini, S., Zucconi, M., et al.: Staging of heavy snorers disease. A proposal. Bull. Eur. Physiopathol. Respir. 19: 590–594, 1983.

Schiavo, G., Montecucco, C.: The structure and mode of action of botulinum and tetanus toxin. Clostridia: Mol. Biol. Pathog., 295–321, 1997.

Schönweiler, R., Wohifahrt, K., Dengler, R., Ptok, M.: Supraglottal injection of botulinum toxin type A in adductor type spasmodic dysphonia with both intrinsic and extrinsic hyperfunction. Laryngoscope 108: 55–63, 1998.

Waller, P. C., Bhopal, R. S.: Is soaring a cause of vascular disease? An epidemiological review. Lancet i: 143–146, 1989.

What is claimed is:

1. A method of temporarily suppressing snoring noises, the method comprising the step of administering intramuscularly an effective amount of uncomplexed Clostridium toxin BoNT/A (botulinum neurotoxin type A) added to a carrier, thereby reducing the snoring.

2. A method according to claim 1, wherein the Clostridium toxin is selected from the group consisting of a recombinant protein and a lyophilized product.

3. A method according to claim 1, wherein the carrier is selected from the group consisting of an aqueous solution, a saline solution, and liposomes.

4. A method of temporarily suppressing snoring noises, the method comprising the step of administering intramuscularly an effective amount of at least one of an uncomplexed Clostridium toxin BoNT/B (botulinum neurotoxin type B), BoNT/C1 (botulinum neurotoxin type C1), BoNT/D (botulinum neurotoxin type D), BoNT/E (botulinum neurotoxin type E), BoNT/F (botulinum neurotoxin type F) and BoNT/G (botulinum neurotoxin type G) added to a carrier, thereby reducing the snoring.

5. A method according to claim 4, wherein the Clostridium toxin is selected from the group consisting of a recombinant protein and a lyophilized product.

6. A method according to claim 4, wherein the carrier is selected from the group consisting of an aqueous solution, a saline solution, and liposomes.

7. A method of temporarily suppressing snoring noises, the method comprising the step of administering intramuscularly an effective amount of an uncomplexed Clostridium toxin TeNT (tetanus neurotoxin) added to a carrier, thereby reducing the snoring.

8. A method according to claim 7, wherein the Clostridium toxin is selected from the group consisting of a recombinant protein and a lyophilized product.

9. A method according to claim 7, wherein the carrier is selected from the group consisting of an aqueous solution, a saline solution, and liposomes.

10. A method of temporarily suppressing snoring noises, the method comprising the step of administering intramuscularly an effective amount of one or more hybrid proteins as a Clostridium toxin, comprised of a light subunit of a Clostridium toxin of the following group and of a heavy subunit of a different Clostridium toxin of the same following group, consisting of: BoNT/A (botulinum neurotoxin type A), BoNT/B (botulinum neurotoxin type B), BoNT/C1 (botulinum neurotoxin type C1), BoNT/D (botulinum neurotoxin type D), BoNT/E (botulinum neurotoxin type E), BoNT/F (botulinum neurotoxin type F), BoNT/G (botulinum neurotoxin type G) and TeNT (tetanus neurotoxin), thereby reducing the snoring.

11. A method according to claim 10, wherein the Clostridium toxin is selected from the group consisting of a recombinant protein and a lyophilized product.

12. A method according to claim 9, wherein the carrier is selected from the group consisting of an aqueous solution, a saline solution, and liposomes.

13. A method of temporarily suppressing snoring noises, the method comprising the step of administering intramuscularly an effective amount of a complex added to a carrier, wherein the complex comprising:

a) a Clostridium toxin or a hybrid protein of a Clostridium toxin; and b) one or more compounds selected from the group consisting of a therapeutically well-tolerated hemagglutinin and a pharmaceutically well-tolerated non-toxin non-hemagglutinating protein of botulinum, thereby reducing the snoring.

14. A method according to claim 13, wherein the complex is of the wild type.

15. A method according to claim 13, wherein the Clostridium toxin is selected from the group consisting of a recombinant protein and a lyophilized product.

16. A method according to claim 13, wherein the carrier is selected from the group consisting of an aqueous solution, a saline solution, and liposomes.

* * * * *